United States Patent
Lozano

(10) Patent No.: US 8,909,342 B2
(45) Date of Patent: Dec. 9, 2014

(54) METHOD FOR TREATING EATING DISORDERS

(75) Inventor: Andres M. Lozano, Toronto (CA)

(73) Assignee: Andres M. Lozano, Toronto, ON (CA)

( * ) Notice: Subject to any disclaimer, the term of this patent is extended or adjusted under 35 U.S.C. 154(b) by 120 days.

(21) Appl. No.: 11/893,077

(22) Filed: Aug. 14, 2007

(65) Prior Publication Data

US 2008/0046013 A1 Feb. 21, 2008

Related U.S. Application Data

(60) Provisional application No. 60/837,633, filed on Aug. 15, 2006.

(51) Int. Cl.
*A61N 1/36* (2006.01)
*A61N 1/05* (2006.01)

(52) U.S. Cl.
CPC ........ *A61N 1/36089* (2013.01); *A61N 1/36085* (2013.01); *A61N 1/0526* (2013.01); *A61N 1/36096* (2013.01); *A61N 1/0529* (2013.01); *A61N 1/0531* (2013.01); *A61N 1/0534* (2013.01); *A61N 1/36082* (2013.01)
USPC ................................... 607/45; 607/3; 607/58

(58) Field of Classification Search
CPC ........... A61N 1/36082; A61N 1/36085; A61N 1/36089; A61N 1/36092; A61N 1/36096; A61N 1/0526; A61N 1/0529; A61N 1/0534
USPC ................. 607/3, 45, 58, 116, 46; 604/890.1; 600/365
See application file for complete search history.

(56) References Cited

U.S. PATENT DOCUMENTS

| | | | |
|---|---|---|---|
| 4,692,147 A | 9/1987 | Duggan | |
| 5,188,104 A | 2/1993 | Wernicke et al. | |
| 5,193,539 A | 3/1993 | Schulman et al. | |
| 5,193,540 A | 3/1993 | Schulman et al. | |
| 5,263,480 A * | 11/1993 | Wernicke et al. | 607/118 |
| 5,312,439 A | 5/1994 | Loeb | |
| 5,324,316 A | 6/1994 | Schulman et al. | |
| 5,405,367 A | 4/1995 | Schulman et al. | |
| 5,752,911 A | 5/1998 | Canedo et al. | |
| 5,782,798 A * | 7/1998 | Rise | 604/500 |
| 5,792,210 A * | 8/1998 | Wamubu et al. | 607/58 |
| 6,051,017 A | 4/2000 | Loeb et al. | |
| 6,132,361 A | 10/2000 | Epstein et al. | |
| 6,425,852 B1 | 7/2002 | Epstein et al. | |
| 6,567,696 B2 | 5/2003 | Voznesensky et al. | |
| 6,592,509 B1 | 7/2003 | Hunter, Jr. | |
| 6,708,064 B2 * | 3/2004 | Rezai | 607/45 |
| 6,712,753 B2 * | 3/2004 | Manne | 600/9 |
| 6,735,474 B1 | 5/2004 | Loeb et al. | |

(Continued)

FOREIGN PATENT DOCUMENTS

| | | |
|---|---|---|
| WO | WO 98/37926 | 9/1998 |
| WO | WO 98/43700 | 10/1998 |
| WO | WO 98/43701 | 10/1998 |

*Primary Examiner* — Eric D. Bertram
*Assistant Examiner* — Pamela M Bays
(74) *Attorney, Agent, or Firm* — Sim & McBurney

(57) ABSTRACT

A method for the treatment of eating disorders by nerve tissue stimulation and infusion techniques to one or more areas of the brain affecting hunger and satiety; palatability and aversion; hedonism; reward/addiction behavior; mood; anxiety; depression, taste and smell. The invention also comprises methods for the treatment of disorders of these individual behaviors and in particular, disorders of taste and/or smell.

28 Claims, 2 Drawing Sheets

(56) References Cited

U.S. PATENT DOCUMENTS

| | | |
|---|---|---|
| 6,735,475 B1 | 5/2004 | Whitehurst et al. |
| 6,782,292 B2 | 8/2004 | Whitehurst |
| 6,950,707 B2 * | 9/2005 | Whitehurst ............... 607/58 |
| 7,013,177 B1 * | 3/2006 | Whitehurst et al. ......... 607/46 |
| 7,493,171 B1 * | 2/2009 | Whitehurst et al. ......... 607/58 |
| 2002/0151939 A1 * | 10/2002 | Rezai ............... 607/40 |
| 2005/0010262 A1 * | 1/2005 | Rezai et al. ............... 607/46 |
| 2005/0033376 A1 * | 2/2005 | Whitehurst ............... 607/45 |
| 2005/0065574 A1 * | 3/2005 | Rezai ............... 607/45 |
| 2006/0004422 A1 * | 1/2006 | De Ridder ............... 607/45 |
| 2006/0069415 A1 * | 3/2006 | Cameron et al. ......... 607/45 |
| 2007/0100389 A1 * | 5/2007 | Jaax et al. ............... 607/42 |
| 2007/0142874 A1 * | 6/2007 | John ............... 607/45 |

* cited by examiner

METHOD FOR TREATING EATING DISORDERS

CROSS REFERENCE TO RELATED APPLICATIONS

This application claims the benefit of U.S. Provisional Patent Application Ser. No. 60/837,633, filed Aug. 15, 2006, which is hereby incorporated by reference herein its entirety.

FIELD OF THE INVENTION

The present invention relates to the treatment of eating disorders. More specifically, the present invention is directed to the treatment of eating disorders by the use of nerve tissue stimulation and infusion techniques to areas of the brain affecting hunger and satiety; palatability and aversion; hedonism; reward/addiction behavior; mood; anxiety; depression; taste; and smell. The invention is also directed to the treatment of disorders of these behaviors and in particular, disorders of taste and smell.

BACKGROUND OF THE INVENTION

Some people suffer from chronic eating disorders, including anorexia and morbid obesity. The neural circuitry of the brain that controls eating and satiety include neurons in the lateral hypothalamus (feeding) and the ventral medial hypothalamus (satiety). U.S. Pat. Nos. 5,188,104 and 5,263,480 describe the use of electrical stimulation for treating eating disorders where the electrical stimulation was applied to the vagus nerve or to the trigeminal and/or glossopharyngeal nerve.

U.S. Pat. No. 5,782,798 describes a method for treating an eating disorder in a patient by stimulating and providing a drug to the central nervous system, in particular the paraventricular nucleus, lateral hypothalamus or ventral medial hypothalamus.

U.S. Pat. No. 6,950,707 describes a method for preventing an eating disorder in a patient by applying stimulus to the nucleus of the solitary tract.

While the aforementioned can provide some treatment and/or prevention of an eating disorder, the methods are not effective in the long term because they do not address many of the underlying behavioral factors and their underlying neurological causes that create and sustain a variety of eating disorders as well as disorders of those behaviors that contribute to eating disorders. Therefore there remains a need to provide further improvements to treatment methods for eating disorders, and their underlying behaviors, that will further improve the long term success of their efficacy.

SUMMARY

The present invention is an improved method for the treatment of an eating disorder in a patient. In the invention, those areas of the brain that affect hunger and satiety; palatability and aversion; hedonism; reward/addiction behavior; mood; anxiety; depression, taste and smell are targeted for stimulation. The method of the invention uses deep brain stimulation (DBS) by electrical stimulation and/or drug treatment. The method of the invention can be used to target one or more of these areas simultaneously or in any desired sequence and combination. In aspects of the invention a variety of brain areas are targeted for stimulation and in this manner eating disorders as well as specific disorders of these areas can be treated.

In particular for the treatment of eating disorders one or more of the areas that affect hunger and satiety; palatability and aversion; hedonism; reward/addiction behavior; mood; anxiety; depression, taste and small are targeted using deep brain stimulation (DBS) by electrical stimulation and/or drug treatment. Drugs and/or electrical stimulation is provided by means of an implantable signal generator and electrode and/or an implantable pump and catheter. A catheter is surgically implanted into one or more desirable areas of the brain to infuse one or more drugs, and one or more electrodes may be surgically implanted in the brain in the desirable areas to provide electrical stimulation. Drugs may also be provided by conventional oral methods as well or in addition to drug infusion.

In this manner the various behavioral drives for food intake are treated to provide a more well-rounded treatment that is more effective in the long term for a patient. In embodiments of the invention, the method and therapeutic system comprise a surgically implanted device in communication with a predetermined site. The device or stimulation system is operated to stimulate the predetermined site thereby treating the eating disorder, i.e. the various underlying aspects thereof. The device can include a stimulation portion or a probe, for example, an electrode, an electrode assembly (e.g., electrical stimulation lead), pharmaceutical-delivery assembly (e.g., catheters) or combinations of these and/or a signal generator or signal source or pulse generating source (i.e., electrical signal source, chemical signal source, pharmaceutical delivery pump or magnetic signal source). The probe may be coupled to the signal source, pharmaceutical delivery pump, or both which, in turn, is operated to stimulate the predetermined treatment site. Yet further, the probe and the signal generator or source can be incorporated together, wherein the signal generator and probe are formed into a unitary or single unit, such unit may comprise, one, two or more electrodes. These devices are known in the art as microstimulators, for example, Bion™ manufactured by Advanced Bionics Corporation.

In further embodiments of the invention, in addition to electrical and chemical (i.e. drug) stimulation, other types of stimulations can also be used, for example, magnetic, thermal and/or ultrasonic stimulation can be used to modulate the targeted area(s) in a predetermined manner. Magnetic stimulation can be provided by internally implanted probes or by externally applied directed magnetic fields. Thermal stimulation can be provided by using implanted probes that are regulated to produce or emit heat and/or cold temperatures.

According to an aspect of the present invention is a method for the treatment of an eating disorder in a patient, the method comprising providing one or more stimuli to one or more areas of the brain that affect hunger and satiety; palatability and aversion; hedonism; reward/addiction behavior; mood; anxiety; depression; taste and smell.

According to a further aspect of the present invention is the use of an electrical and/or pharmacological stimuli in one or more areas of a brain of a patient that affect hunger and satiety; palatability and aversion; hedonism; reward/addiction behavior; mood; anxiety; depression, taste and smell.

According to yet another aspect of the present invention is a method for the treatment of an eating disorder in a patient, the method comprising implanting a pump and a catheter having a proximal end coupled to the pump and having a discharge portion for infusing therapeutic dosages of the one or more drugs into a predetermined infusion site in brain tissue that affects one or more of hunger and satiety; palatability and aversion; hedonism; reward/addiction behavior; mood; anxiety; depression, taste and smell.

According to yet another aspect of the present invention is a method for the treatment of an eating disorder in a patient, the method comprising implanting a signal generator and having a stimulation portion into a predetermined infusion site in brain tissue that affects one or more of hunger and satiety; palatability and aversion; hedonism; reward/addiction behavior; mood; anxiety; depression, taste and smell.

A method of treating a mood disorder and/or anxiety disorder comprising the steps of: surgically implanting an electrode in communication with a predetermined site selected from the group consisting of hippocampus, insula, caudate, orbitofrontal cortex, anterior cingulated cortex, parahippocampal and hippocampal formation, thalamus, precuneus, putamen and cerebellum, ventromedial prefrontal cortex, dorsolateral prefrontal cortex and inferior parietal lobule, insular and orbitofrontal cortex, nucleus accumbens, septal area, intralaminar nuclei of thalamus, PAG, PVG, amygdale, periaqueductal gray, periventricular grey, intralaminal thalamic nuclei, parietal operculum, parainsular cortex and combinations thereof; coupling the electrode to a pulse generating source; and generating an electrical signal with the pulse generating source wherein said signal electrically stimulates the predetermined site thereby treating the mood disorder and/or anxiety disorder.

In aspects of the invention, these sites as described herein can additionally be coupled with the targeting of one or more of the vagus nerve, trigeminal nerve, glossopharyngeal nerve, paraventricular nucleus, lateral hypothalamus, ventral medial hypothalamus and nucleus of the solitary tract. Still in other aspects of the invention the method may exclude the targeting of the vagus nerve, trigeminal nerve, glossopharyngeal nerve, paraventricular nucleus, lateral hypothalamus, ventral medial hypothalamus and nucleus of the solitary tract.

In aspects of the invention the method is used to simultaneously trigger one or more sites in combination and/or in sequence to provide a more effective method for treating eating disorders as well as taste and smell disorders.

In a further aspect of the invention is a method for the treatment of an addiction, a taste and/or smell disorder in a patient, the method comprising providing one or more stimuli to one or more areas of the brain that affect reward and addiction, taste and/or smell.

According to a further aspect of the present invention is the use of an electrical and/or pharmacological stimuli in one or more areas of a brain of a patient that affect addiction, taste and/or smell.

According to still another aspect of the present invention is a method for the treatment of addiction and addiction behaviors (compulsive gambling, alcohol, nicotine, food, drugs including but not limited to cocaine, opiates, heroin hallucinogens and disorders of smell and/or taste by the targeting of taste and/or smell pathways. In aspects, brain areas that could be targeted to control reward and/or addiction behaviors include but are not limited to, the nucleus accumbens, the cingulate gyrus, the amygdala, the hypothalamus, the periventricular and periaqueductal gray, the inferior thalamic peduncle, the nucleus of the solitary tract, the anterior limb of the internal capsule, the orbitofrontal cortices, the prefrontal cortex, the dorsolateral prefrontal cortex and the intralaminar and dorsomedial thalamic nuclei.

According to a further aspect of the invention is a method for the treatment of one or more undesirable behaviors and/or disorders in a patient, the method comprising the use of deep brain stimulation (DBS) to target areas of the brain responsible for said undesirable behavior and/or disorder.

In aspects the undesirable behavior is an eating disorder, and the method comprises providing one or more stimuli to one or more areas of the brain that affect hunger and satiety; palatability and aversion; hedonism; reward/addiction behavior; mood; anxiety; depression; and taste and smell.

In aspects the eating disorder is selected from the group consisting of overeating resulting in obesity, bulimia, compulsive eating, pica, insufficient eating leading to anorexia, improper eating resultant of diabetes, and combinations thereof.

In aspects the undesirable behavior is an addiction and/or addiction behavior selected from the group consisting of compulsive gambling, alcohol, nicotine, food, drugs and disorders of smell and/or taste, the method comprising providing one or more stimuli to one or more areas of the brain that affect said behaviors.

In aspects the disorder is of smell and/or taste and said method comprises providing one or more stimuli to one or more areas of the brain involved in taste and/or smell pathways.

In aspects the stimulation may be applied to areas affecting taste selected from the group consisting of the ventral tegmental area, ventral striatum containing the nucleus accumbens, frontal operculum, dorsal insula, orbitofrontal cortex, amygdale and combinations thereof.

In aspects of the invention the stimulation may be applied to areas of the brain and nervous tissue selected from the group consisting of hippocampus, insula, caudate, orbitofrontal cortex, anterior cingulated cortex, parahippocampal and hippocampal formation, thalamus, precuneus, putamen and cerebellum, ventromedial prefrontal cortex, dorsolateral prefrontal cortex and inferior parietal lobule, insular and orbitofrontal cortex, nucleus accumbens, septal area, intralaminar nuclei of thalamus, PAG, PVG, amygdale, periaqueductal gray, periventricular grey, intralaminal thalamic nuclei, parietal operculum, parainsular cortex and combinations thereof.

In aspects of the invention the method further comprises applying stimulation in various combinations to one or more of the vagus nerve, trigeminal nerve, glossopharyngeal nerve, paraventricular nucleus, lateral hypothalamus, ventral medial hypothalamus and nucleus of the solitary tract.

In aspects of the invention, deep brain stimulation is selected from the group consisting of electrical stimulation, pharmacological stimulation, magnetic stimulation, thermal stimulation, ultrasonic stimulation and combinations thereof.

In aspects of the invention electrical stimulation may be implemented by providing pulses to electrodes targeting areas of said brain, said pulses having amplitudes of about 0.1 to about 20 volts, pulse widths varying from about 0.02 to about 500 microseconds, and frequencies varying from about 1 to about 2500 Hz.

In aspects of the invention the method comprises the use of one or more pharmacological agents concurrently with a selected stimulation and/or following a selected stimulation as described herein.

In aspects of the invention the method comprises combinations of electrical stimulation and infusion of pharmacological agents at multiple brain sites. In further aspects of the invention the stimulation is provided in one or more of the following manners:
  a) intermittently,
  b) intermittently with concurrent continuous pharmacological agent infusion;
  c) alternating with pharmacological agent infusion;
  d) simultaneously to one or more selected areas;
  e) sequentially to one or more areas; and
  f) a combination of d) and e).

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE PREFERRED EMBODIMENTS OF THE INVENTION

The present invention is the treatment of undesirable behaviors and/or disorders in a patient using deep brain stimulation (DBS) targeted at one or more areas of the brain responsible or contributing to the undesirable behavior and/or disorder.

The present invention in aspects is the use of stimulation to one or more areas of the brain that affects hunger and satiety; palatability and aversion; hedonism; reward/addiction behavior; mood; anxiety; depression, taste and smell in order to effectively treat an eating disorder and components thereof. In this manner a variety of the behaviors that contribute to an eating disorder are treated and controlled in a more effective manner than previously known. Thus the invention is a variety of method using deep brain stimulation (DBS) by electrical stimulation and/or drug treatment to treat undesirable behaviors as herein described.

The method of the invention is useful to control food intake in a patient and thus used to treat eating disorders in such patients. Eating disorders can include but not be limited to overeating resulting in obesity, bulimia, compulsive eating, pica, insufficient eating leading to anorexia, improper eating resultant of diabetes, and abnormalities in the perception of taste (ageusia/dysgeusia) that lead to abnormal eating patterns. It is also understood to one of skill in the art that eating disorders may also involve disorders of taste and smell and thus the invention also encompasses methods of treating taste and smell disorders.

Figure 1A:
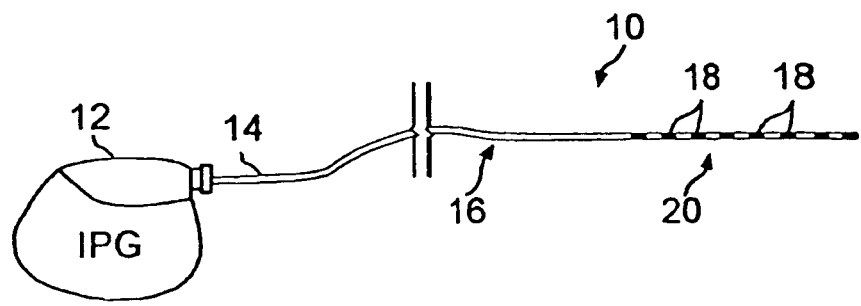
FIGS. 1A and 1B illustrate example electrical stimulation systems.
Figure 1B:
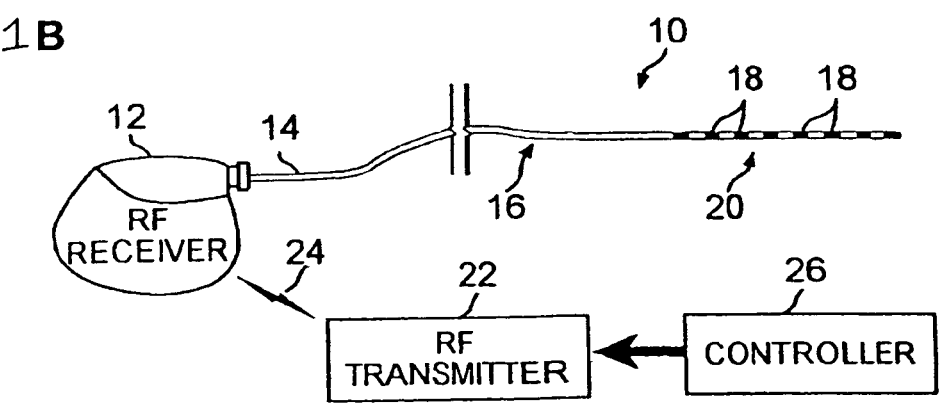

FIGS. 1A and 1B illustrate representative example electrical stimulation systems 10 used to provide deep brain stimulation. Stimulation system 10 generates and applies a stimulus to a target area of the brain or is in communication with the target area of the brain, for example, insular cortex and/or caudate. In general, the stimulation system 10 includes an implantable pulse generating source, such as an electrical stimulation source 12 and an implantable stimulation portion, for example an electrode. In certain embodiments the electrode is comprised within an electrical stimulation lead 14. In operation, both of these primary components are implanted in the person's body. Stimulation source 12 is coupled to a connecting portion 16 of electrical stimulation lead 14. Stimulation source 12 controls the electrical signals transmitted to electrodes 18 located on a stimulating portion 20 of electrical stimulation lead 14, located adjacent the target brain tissue, according to suitable signal parameters (e.g., duration, intensity, frequency, etc.). A doctor, the patient, or another user of stimulation source 12 may directly or indirectly input signal parameters for controlling the nature of the electrical stimulation provided.

In an embodiment shown in FIG. 1A, stimulation source 12 includes an implantable pulse generator (IPG). One of skill in the art is aware that any commercially available implantable pulse generator can be used in the present invention, as well as a modified version of any commercially available pulse generator. Thus, one of skill in the art would be able to modify an IPG to achieve the desired results. An exemplary IPG is one that is manufactured by Advanced Neuromodulation Systems, Inc. Another example of an IPG is shown in FIG. 1B, which shows stimulation source 12 including an implantable wireless receiver. An example of a wireless receiver may be one manufactured by Advanced Neuromodulation Systems, Inc., such as the Renew™ System. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. An example wireless transmitter 122 may be one manufactured by Advanced Neuromodulation Systems, Inc., such as the Renew™ System.

The system or device 10 used in the present invention may include but not be limited to those described in U.S. Pat. Nos. 4,692,147, 5,193,539, 5,193,540, 5,312,439, 5,324,316, 5,405,367, 6,051,017 6,735,475; 6,735,474 and 6,782,292 and in WO 98/37926, WO 98/43700 and WO 98/43701 (the disclosures of which are incorporated herein by reference in their entirety).

Electrical stimulation of the desired area or areas of nerve tissue may be implemented by providing pulses to the electrodes having amplitudes of about 0.1 to about 20 volts, pulse widths varying from about 0.02 to about 500 microseconds, and frequencies varying from about 1 to about 2500 Hz. The appropriate stimulation pulses are generated by device as programmed. The type of stimulation administered by device to the brain depends on the specific location at which the electrodes of tube are surgically implanted. These stimulations can be provided at multiple sites as described herein. That is, they can be provided simultaneously to more than one site, or sequentially as required or a combination of both. The stimulation be provided pre-programmed on a daily basis or patient activated or on a closed feedback system in response to a physiological parameter such as for example but not limited to glucose or insulin levels.

The appropriate stimulation may be applied to the following areas of the brain and nervous tissue: hippocampus, insula, caudate, orbitofrontal cortex, anterior cingulated cortex, parahippocampal and hippocampal formation, thalamus, precuneus, putamen and cerebellum, ventromedial prefrontal cortex, dorsolateral prefrontal cortex and inferior parietal lobule, insular and orbitofrontal cortex, nucleus accumbens, septal area, intralaminar nuclei of thalamus, PAG, PVG, amygdale, periaqueductal gray, periventricular grey, intralaminal thalamic nuclei, parietal operculum, parainsular cortex and combinations thereof with the effect of the stimulation on that portion of the brain is or treatment of an eating disorder involving one or more behaviors provided as follows:

hunger and satiety;
palatability and aversion;
hedonism;
reward/addiction behavior;
mood;
anxiety;
taste;
smell; and
depression.

In aspects of the invention, the areas for applying stimulation in addition to those encompassed supra may also further include in various combinations the vagus nerve, trigeminal nerve, glossopharyngeal nerve, paraventricular nucleus, lateral hypothalamus, ventral medial hypothalamus and nucleus of the solitary tract. Alternatively, the methods of the invention may exclude one or all of these areas.

A microprocessor within the device implemented to provide the stimulus is programmed so that the desired stimulation can be delivered to the specific brain sites described. Alternatively, the patient may control the stimulation manually.

Figure 2:
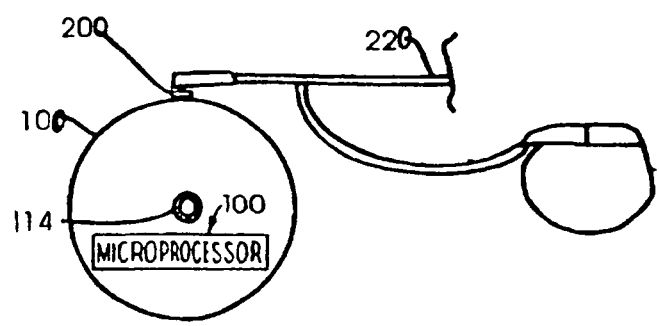
FIG. 2 is a representative diagrammatic illustration of a combined catheter and electrode implanted in a brain according to an embodiment of the present invention, and a signal generator and pump coupled to the combined catheter and electrode.

The method of the invention can use a combination of electrical stimulation and infusion of a drug (pharmacological substance). Infusion and electrical stimulation is shown in FIG. 2 as a combined catheter and electrode and can be applied separately or simultaneously and repeated as required/desired. Referring to FIG. 2, a system or device 100 made in accordance with an embodiment of the invention may be implanted below the skin of a patient. The device has a port 114 into which a hypodermic needle can be inserted through the skin to inject a quantity of a liquid agent, such as a medication or drug. The liquid agent is delivered from device 100 through a catheter port 200 into a catheter 220. Catheter 220 is positioned to deliver the agent to specific infusion sites in a brain. Device 100 may take the form of a device shown in U.S. Pat. No. 4,692,147 (the contents of which is incorporated by reference).

Such combination of electrical and pharmacological agent may increase the effectiveness of the electrical stimulation method of the present invention, and thus it may be desirable to combine electrical stimulation with chemical stimulation to treat the eating disorder. For example, infusion alone can be applied from a certain time, infusion and stimulation can both be applied from a different time, and stimulation alone can be applied from yet a different time to the first two. This is understood to be determined by the medical practitioner for the patient as is understood by one of skill in the art. In addition to electrical and chemical stimulation, other types of stimulations can also be used, for example, magnetic, thermal and/or ultrasonic stimulation can be used. Magnetic stimulation can be provided by internally implanted probes or by externally applied directed magnetic fields, for example, U.S. Pat. Nos. 6,592,509; 6,132,361; 5,752,911; and 6,425,852, (each of which is incorporated herein in its entirety). Thermal stimulation can be provided by using implanted probes that are regulated for heat and/or cold temperatures which can stimulate or inhibit neuronal activity, for example, U.S. Pat. No. 6,567,696 (incorporated herein by reference in its entirety).

The electrical stimulation might be applied intermittently to a background of continuous or modulated infusion of one or more drugs. An example of how this might be used, considering the therapy for morbid obesity, is programming the pump to deliver a background infusion of drug to control appetite and programming an electrical stimulation device to periodically apply electrical stimulation to increase appetite suppression or some other eating aspect. The periods of stimulation might coincide with normal periods of the day when appetite increases, such as meal times. Alternatively, periods of stimulation may be triggered by a signal telemetered to the implanted device by the patient at times when the patient experiences increased hunger. The patient would use a portable computing device to trigger the implanted device. When treating anorexia, the patient might activate hunger inducing or satiety reducing stimulus or infusion in order to eat meals specified by a prescribed diet. Still another approach would be to alternate the application of electrical stimulation and drug infusion, a continuous control of appetite is achieved by activating different populations of neurons as described herein with respect to the various behaviors for less than continuous periods of time. This method advantageously may reduce the risk of damaging one population of neurons through overactivation. Electrical stimulation or drug infusions may be alternatively delivered to multiple sites in the brain as desired.

Combinations of electrical stimulation and infusion at multiple sites may be used to control different aspects of hunger and satiety; palatability and aversion; hedonism; reward/addiction behavior; mood; anxiety; depression, taste and smell each of which plays a role in eating disorders in certain individuals. Infusion or stimulation at one site may selectively control hunger for fat while stimulation or infusion at another site could be used to control hunger for carbohydrates. In this case, the infusion and stimulation timing diagrams (not shown) may be quite elaborate with varying degrees of synchronization.

The present invention may be implemented by providing different drug dosages from about a zero dosage to about a 1.0 ml dosage with about 0.1 ml increments between choices. One of skill in the art could determine suitable dosages. The time interval between dosages can be selected between one and twelve hours in seven choices. The selected dosage and interval of a drug is then delivered to the portions of the brain identified as being involved in hunger and satiety; palatability and aversion; hedonism; reward/addiction behavior; mood; anxiety; depression; taste; and smell.

Suitable drugs for use in the present invention are those that can affect those brain areas involved in hunger and satiety; palatability and aversion; hedonism; reward/addiction behavior; mood; anxiety; depression; taste; and smell. One of skill in the art would understand that this may include but not be limited to agents that act as agonists or antagonists to the transmitters acting in a particular place in the brain. Agents that block the reuptake or enzymatic breakdown of those transmitters or cause them to be released from their synaptic vesicles could be substituted for agonists. Enzymes that would speed up the breakdown of transmitters could be used as an alternative to antagonists. Agents, such as Bombesin, which have a generalized effect may be infused into the ventricles or hypothalamus. More specifically suitable drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts and anesthetics (e.g., lidocane) may also be used in combination with electrical stimulation.

Delivery of the drugs to the specific target locations described supra will result in the fewest neurological side effects since the effects of the drugs on other neurons subserving other functions is minimized. Exemplary drugs with their ranges of dosages and drug concentrations for some of the classes of drugs are identified in the following list: Adrenergic Agonist Clonidine HCL 10 nM-50 m$\mu$M Ephedrine HCL 10 nM-50 m$\mu$M Norepinephrine 10 nM-50 m$\mu$M Adrenergic Antagonists Verapamil HCL 10 nM-50 m$\mu$M Propranolol 10 nM-50 m$\mu$M Urapidil HCL 10 nM-50 m$\mu$M Opioid Agonist Morphine 0.1-500 m$\mu$M Opioid Antagonist Naloxone 0.1-500 m$\mu$M Serotonin Agonist Buspirone HCL 10 nM-50 m$\mu$M L-methyl serotonin 10 nM-50 m$\mu$M Serotonin Antagonist (−) Sulpiride 0.05-1 m$\mu$M spiperone HCL 0.1-10 m$\mu$M Propranolol HCL 0.05-1 m$\mu$M Pancreatic Polypeptide NPY 20-300 picoM Agonist PYY 2 picoM to 10 m$\mu$M Pancreatic Polypeptide Leptin 2 picoM to 10 m$\mu$M Antagonist GABA Agonists baclofen 0.1-10 m$\mu$M muscinol HBr 100-500 m$\mu$M GABA Antagonists Gabazine 1-50 m$\mu$M Saclofen 0.5-25 m$\mu$M Bicuulline 1-100 m$\mu$M picrotoxin 10-100 m$\mu$M Dopamine Antagonist (+) apomorphone HCL 5-20 m$\mu$M spiperone HCL 0.1-10 m$\mu$M haloperidol 10-100 m$\mu$M (−) Sulpiride 0.05-1 m$\mu$M Dopamine Agonist methanesulfonate 1-10 m$\mu$M Dopamine Agonist (−) apomorphine 10-30 m$\mu$M (cont.) pergolide Glucagon Agonist GLP-1 0.05-500 m$\mu$M Glucagon Antagonist exendin (9-39) 0.01-500 m$\mu$M Anesthetic Lidocaine hydrochloride 5-20 m$\mu$M.

By using the foregoing techniques for electrical stimulation or simultaneously drug infusion and electrical stimulation, eating disorders and the physiological components/triggers/behaviors thereof can be controlled with a degree of accuracy previously unattainable.

In a further embodiment of the invention, the method can be used for the treatment of addiction and addiction behaviors (compulsive gambling, alcohol, nicotine, food, drugs including but not limited to cocaine, opiates, heroin hallucinogens and disorders of smell and/or taste by the targeting of taste and/or smell pathways). Brain areas that could be targeted to control reward and/or addiction behaviors include but are not limited to, the nucleus accumbens, the cingulate gyrus, the amygdala, the hypothalamus, the periventricular and periaqueductal gray, the inferior thalamic peduncle, the nucleus of the solitary tract, the anterior limb of the internal capsule, the orbitofrontal cortices, the prefrontal cortex, the dorsolateral prefrontal cortex, the intralaminar and dorsomedial thalamic nuclei and combinations thereof.

In a further embodiment of the invention, the method can be used for the treatment of disorders of smell and/or taste by the targeting of taste and/or smell pathways. Smell and taste disorders are common in the general population, with loss of smell occurring more frequently. These disorders may have a substantial impact on quality of life and may represent significant underlying disease. People may have difficulty recognizing smell versus taste dysfunction and frequently confuse the concepts of "flavor" and "taste." While the most common causes of smell disturbance are nasal and sinus disease, upper respiratory infection and head trauma, frequent causes of taste disturbance include oral infections, oral appliances (e.g., dentures), dental procedures and Bell's palsy. Medications can also interfere with smell and taste. In addition, advancing age has been associated with a natural impairment of smell and taste ability.

The human sense of smell depends on the functioning of not only cranial nerve I (olfactory nerve) but also portions of cranial nerve V (trigeminal nerve). Smell receptors are located within the olfactory neuroepithelium, a region of tissue found over the cribform plate, the superior septum and a segment of the superior turbinate. The free nerve endings of cranial nerve V are located diffusely throughout the nasal respiratory epithelium, including regions of the olfactory neuroepithelium. Any of these areas alone or in combination can be targeted in the method of the invention.

Many nerves are responsible for transmitting taste information to the brain. Because of these multiple pathways, total loss of taste (ageusia) is rare. As in the olfactory system, somatosensory sensations are induced through trigeminal nerve fibers in the tongue and oral cavity. Taste receptors are found within taste buds located not only on the tongue but also on the soft palate, pharynx, larynx, epiglottis, uvula and first one third of the esophagus. The method of the present invention can be used to target areas involved in taste such as but not limited to the ventral tegmental area, ventral striatum containing the nucleus accumbens, frontal operculum, dorsal insula, orbitofrontal cortex and amygdale.

In summary, the present invention provides an effective method and system for the treatment of eating disorders, addiction smell and/or taste disorders. The method and system of the invention is also useful for the treatment of the underlying behaviors involved in eating disorders.

Those skilled in that art will recognize that the preferred embodiments may be altered or amended without departing from the true spirit and scope of the invention, as defined in the accompanying claims.

The invention claimed is:

1. A method for the indirect treatment of an eating disorder in a patient wherein the eating disorder involves one or more behaviors and/or disorders selected from the group consisting of mood and/or anxiety disorders, taste and/or smell disorders, and reward and/or addiction behaviors, the method comprising:
   (a) identifying a patient with an eating disorder;
   (b) determining whether the eating disorder involves a mood and/or anxiety disorder, and if the eating disorder is determined to involve a mood and/or anxiety disorder, then applying deep brain stimulation (DBS) directly to one or more areas of the brain and/or nervous tissue responsible for said mood and/or anxiety disorder selected from the group consisting of the hippocampus, the insula, the caudate, the orbitofrontal cortex, the anterior cingulated cortex, the parahippocampal formation, the hippocampal formation, the thalamus, the precuneus, the putamen, the cerebellum, the ventromedial prefrontal cortex, the dorsolateral prefrontal cortex, the inferior parietal lobule, the insular cortex, the nucleus accumbens, the septal area, the intralaminar nuclei of the thalamus, the periaqueductal gray, the periventricular grey, the amygdala, the parietal operculum, the parainsular cortex and combinations thereof, wherein the direct stimulation of the one or more areas of the brain and/or nervous tissue responsible for said mood and/or anxiety behavior directly treats the mood and/or anxiety behavior and indirectly treats the eating disorder; and (c) determining whether the eating disorder involves a taste and/or smell disorder, and if the eating disorder is determined to involve a taste and/or smell disorder, then applying DBS directly to one or more areas of the brain and/or nervous tissue responsible for said taste and/or smell disorders selected from the group consisting of the ventral tegmental area, the ventral striatum, the nucleus accumbens, the frontal operculum, the dorsal insula, the orbitofrontal cortex, the amygdala and combinations thereof, wherein the direct stimulation of the one or more areas of the brain and/or nervous tissue responsible for said taste and/or smell disorder directly treats the taste and/or smell disorder and indirectly treats the eating disorder; and (d) determining whether the eating disorder involves a reward and/or addiction behavior, and if the eating disorder is determined to involve a reward and/or addiction behavior, then applying DBS directly to one or more areas of the brain and/or nervous tissue responsible for said reward and/or addiction behaviors selected from the group consisting of the nucleus accumbens, the cingulate gyrus, the amygdala, the hypothalamus, the periventricular gray, the periaqueductal gray, the interior thalamic peduncle, the nucleus of the solitary tract, the anterior limb of the internal capsule, the orbitofrontal cortices, the prefrontal cortex, the dorsolateral prefrontal cortex, the intralaminar thalamic nucleus, the dorsomedial thalamic nucleus and combinations thereof, wherein the direct stimulation of the one or more areas of the brain and/or nervous tissue responsible for the reward and/or addiction behavior directly treats the reward and/or addiction behavior and indirectly treats the eating disorder.

2. The method of claim 1, wherein said eating disorder is selected from the group consisting of overeating resulting in obesity, bulimia, compulsive eating, pica, insufficient eating leading to anorexia, improper eating resultant of diabetes, abnormalities in the perception of taste and combinations thereof.

3. The method of claim 1 or 2, wherein said method further comprises applying stimulation in various combinations to one or more of the vagus nerve, the trigeminal nerve, the glossopharyngeal nerve, the paraventricular nucleus, the lateral hypothalamus, the ventral medial hypothalamus and the nucleus of the solitary tract.

4. The method of claim 1 or 2, wherein the reward and/or addiction behavior is selected from the group consisting of compulsive gambling, alcohol, nicotine, food, drugs and combinations thereof.

5. The method of claim 4, wherein said method further comprises applying stimulation in various combinations to one or more of the vagus nerve, the trigeminal nerve, the glossopharyngeal nerve, the paraventricular nucleus, the lateral hypothalamus, the ventral medial hypothalamus and the nucleus of the solitary tract.

6. The method of claim 4, wherein said DBS is selected from the group consisting of electrical stimulation, pharmacological stimulation, magnetic stimulation, thermal stimulation, ultrasonic stimulation and combinations thereof.

7. The method of claim 6, wherein said electrical stimulation is implemented by providing pulses to electrodes targeting areas of said brain, said pulses having amplitudes of about 0.1 to about 20 volts, pulse widths varying from about 0.02 to about 500 microseconds, and frequencies varying from about 1 to about 2500 Hz.

8. The method of claim 6, wherein said method comprises the use of one or more pharmacological agents concurrently with a selected stimulation and/or following a selected stimulation.

9. The method of claim 8, wherein said method comprises combinations of electrical stimulation and infusion of pharmacological agents at multiple brain sites.

10. The method of claim 9, wherein said stimulation is provided in one or more of the following:
a) intermittently,
b) intermittently with concurrent continuous pharmacological agent infusion;
c) alternating with pharmacological agent infusion;
d) simultaneously to one or more selected areas;
e) sequentially to one or more areas; and
f) a combination of d) and e).

11. The method of claim 1 or 2, wherein said DBS is selected from the group consisting of electrical stimulation, pharmacological stimulation, magnetic stimulation, thermal stimulation, ultrasonic stimulation and combinations thereof.

12. The method of claim 11, wherein said electrical stimulation is implemented by providing pulses to electrodes targeting areas of said brain, said pulses having amplitudes of about 0.1 to about 20 volts, pulse widths varying from about 0.02 to about 500 microseconds, and frequencies varying from about 1 to about 2500 Hz.

13. The method of claim 11, wherein said method comprises the use of one or more pharmacological agents concurrently with a selected stimulation and/or following a selected stimulation.

14. The method of claim 13, wherein said method comprises combinations of electrical stimulation and infusion of pharmacological agents at multiple brain sites.

15. The method of claim 14, wherein said stimulation is provided in one or more of the following:
a) intermittently,
b) intermittently with concurrent continuous pharmacological agent infusion;
c) alternating with pharmacological agent infusion;
d) simultaneously to one or more selected areas;
e) sequentially to one or more areas; and
f) a combination of d) and e).

16. A method for the indirect treatment of an eating disorder in a patient wherein the eating disorder involves one or more behaviors and/or disorders selected from the group consisting of mood and/or anxiety disorders, taste and/or smell disorders, and reward and/or addiction behaviors, the method comprising:
(a) identifying a patient with an eating disorder;
(b) determining whether the eating disorder involves a mood and/or anxiety disorder, and if the eating disorder is determined to involve a mood and/or anxiety disorder, then applying deep brain stimulation (DBS) directly to one or more areas of the brain and/or nervous tissue responsible for said mood and/or anxiety disorder selected from the group consisting of the hippocampus, the insula, the caudate, the orbitofrontal cortex, the anterior cingulated cortex, the parahippocampal formation, the hippocampal formation, the thalamus, the precuneus, the putamen, the cerebellum, the ventromedial prefrontal cortex, the dorsolateral prefrontal cortex, the inferior parietal lobule, the insular cortex, the nucleus accumbens, the septal area, the intralaminar nuclei of the thalamus, the periaqueductal gray, the periventricular grey, the amygdala, the parietal operculum, the parainsular cortex and combinations thereof, wherein the direct stimulation of the one or more areas of the brain and/or nervous tissue responsible for said mood and/or anxiety behavior directly treats the mood and/or anxiety behavior and indirectly treats the eating disorder; and (c) determining whether the eating disorder involves a taste and/or smell disorder, and if the eating disorder is determined to involve a taste and/or smell disorder, then applying DBS directly to one or more areas of the brain and/or nervous tissue responsible for said taste and/or smell disorders selected from the group consisting of the ventral tegmental area, the ventral striatum, the nucleus accumbens, the frontal operculum, the dorsal insula, the orbitofrontal cortex, the amygdala and combinations thereof, wherein the direct stimulation of the one or more areas of the brain and/or nervous tissue responsible for said taste and/or smell disorder directly treats the taste and/or smell disorder and indirectly treats the eating disorder; and (d) determining whether the eating disorder involves a reward and/or addiction behavior, and if the eating disorder is determined to involve a reward and/or addiction behavior, then applying DBS directly to one or more areas of the brain and/or nervous tissue responsible for said reward and/or addiction behaviors selected from the group consisting of the nucleus accumbens, the cingulate gyrus, the amygdala, the hypothalamus, the periventricular gray, the periaqueductal gray, the interior thalamic peduncle, the nucleus of the solitary tract, the anterior limb of the internal capsule, the orbitofrontal cortices, the prefrontal cortex, the dorsolateral prefrontal cortex, the intralaminar thalamic nucleus, the dorsomedial thalamic nucleus and combinations thereof, wherein the direct stimulation of the one or more areas of the brain and/or nervous tissue responsible for the reward and/or addiction behavior directly treats the reward and/or addiction behavior and indirectly treats the eating disorder, wherein said DBS is electrical stimulation and wherein said electrical stimulation is implemented by providing pulses to electrodes directly targeting said one or more areas of the brain and/or nervous tissue, said pulses having pulse widths varying from about 0.02 to about 500 microseconds.

17. The method of claim 16, wherein said eating disorder is selected from the group consisting of overeating resulting in obesity, bulimia, compulsive eating, pica, insufficient eating leading to anorexia, improper eating resultant of diabetes, abnormalities in the perception of taste and combinations thereof.

18. The method of claim 16 or 17, wherein said method further comprises applying stimulation in various combinations to one or more of the vagus nerve, the trigeminal nerve, the glossopharyngeal nerve, the paraventricular nucleus, the lateral hypothalamus, the ventral medial hypothalamus and the nucleus of the solitary tract.

19. The method of claim 16 or 17, wherein said pulses have amplitudes of about 0.1 to about 20 volts and frequencies varying from about 1 to about 2500 Hz.

20. The method of claim 16 or 17, wherein the reward and/or addiction behavior is selected from the group consisting of compulsive gambling, alcohol, nicotine, food, drugs and combinations thereof.

21. The method of claim 20, wherein said method further comprises applying stimulation in various combinations to one or more of the vagus nerve, the trigeminal nerve, the glossopharyngeal nerve, the paraventricular nucleus, the lateral hypothalamus, the ventral medial hypothalamus and the nucleus of the solitary tract.

22. The method of claim 16 or 17, wherein said method comprises the use of one or more pharmacological agents concurrently with said electrical stimulation and/or following said electrical stimulation.

23. The method of claim 22, wherein said method comprises combinations of electrical stimulation and infusion of pharmacological agents at multiple brain sites.

24. The method of claim 23, wherein said electrical stimulation is provided in one or more of the following:
 a) intermittently,
 b) intermittently with concurrent continuous pharmacological agent infusion;
 c) alternating with pharmacological agent infusion;
 d) simultaneously to one or more selected areas;
 e) sequentially to one or more areas; and
 f) a combination of d) and e).

25. The method of claim 1, 2, 16 or 17, wherein said stimulation is provided pre-programmed or patient activated or is provided on a closed feedback system.

26. The method of claim 25, wherein said stimulation is patient activated and is applied at meal times.

27. The method of claim 25, wherein said stimulation is provided on a closed feedback system in response to a physiological parameter.

28. The method of claim 27, wherein said physiological parameter is selected from glucose levels and insulin levels.

* * * * *